United States Patent [19]
Machson

[11] Patent Number: 5,732,410
[45] Date of Patent: Mar. 31, 1998

[54] FACE SHIELD HAVING CLOSEABLE DRAPE

[76] Inventor: Roger Machson, 455 Coloma, Sausalito, Calif. 94965

[21] Appl. No.: 738,977

[22] Filed: Oct. 24, 1996

[51] Int. Cl.$^6$ .................... A61F 9/04; A42B 1/06
[52] U.S. Cl. ........................... 2/9; 2/11; 128/857
[58] Field of Search .................. 2/6.3, 6.7, 6.4, 2/15, 11, 9, 10, 6.5, 424, 468, 173; 128/857, 858, 917

[56] References Cited

U.S. PATENT DOCUMENTS

| | | | |
|---|---|---|---|
| 1,820,237 | 8/1931 | Malcom | 2/9 |
| 2,262,449 | 11/1941 | Buegeleisen | 2/9 |
| 2,686,912 | 8/1954 | Shipman | 2/9 |
| 4,852,185 | 8/1989 | Olson | 2/9 |
| 4,884,296 | 12/1989 | Nix, Jr. | 2/11 |
| 5,113,528 | 5/1992 | Burke, Jr. et al. | |
| 5,440,760 | 8/1995 | Highsmith | 2/9 |

Primary Examiner—C. D. Crowder
Assistant Examiner—Larry D. Worrell, Jr.
Attorney, Agent, or Firm—Larry D. Johnson

[57] ABSTRACT

A face shield apparatus to prevent bodily fluids and foreign materials from splashing into the user's face in medical situations. In non-medical use, this invention relates generally to preventing non-impact exposure from liquid splash, dirt and dust. The apparatus includes a transparent face portion providing a flat viewing area in front of the user's eyes, a forehead barrier portion to protect the user against splash to the eyes from above, a head strap portion to fit around the user's head to hold the face shield in place, and a drape portion to protect against splash coming up under the shield. This drape portion features a fluid-impermeable fabric below the plastic to cover the user's chin and upper neck. Light pressure to the bottom of the fluid barrier fabric closes the fabric under the user's chin with fasteners.

5 Claims, 5 Drawing Sheets

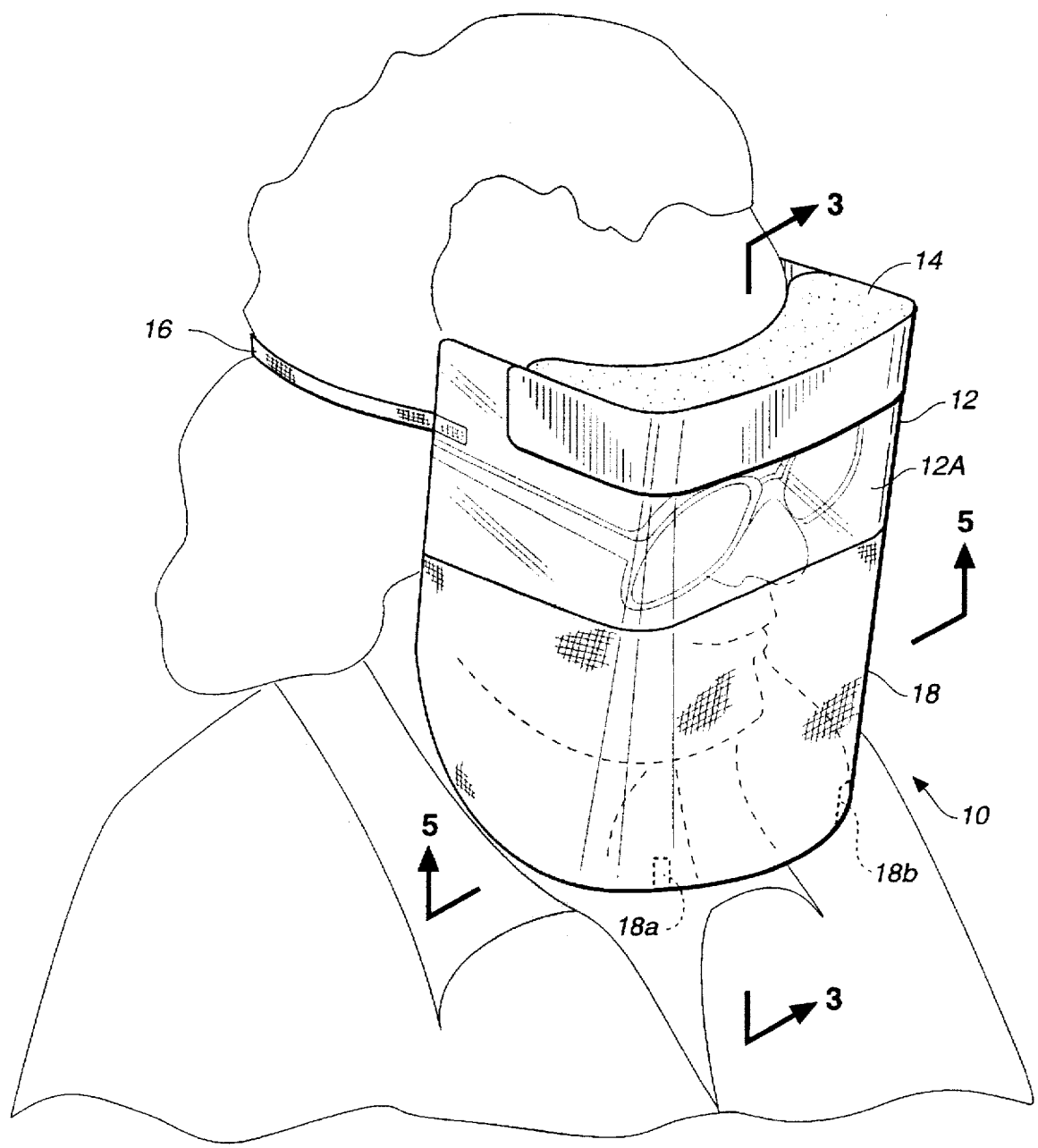
FIG._1

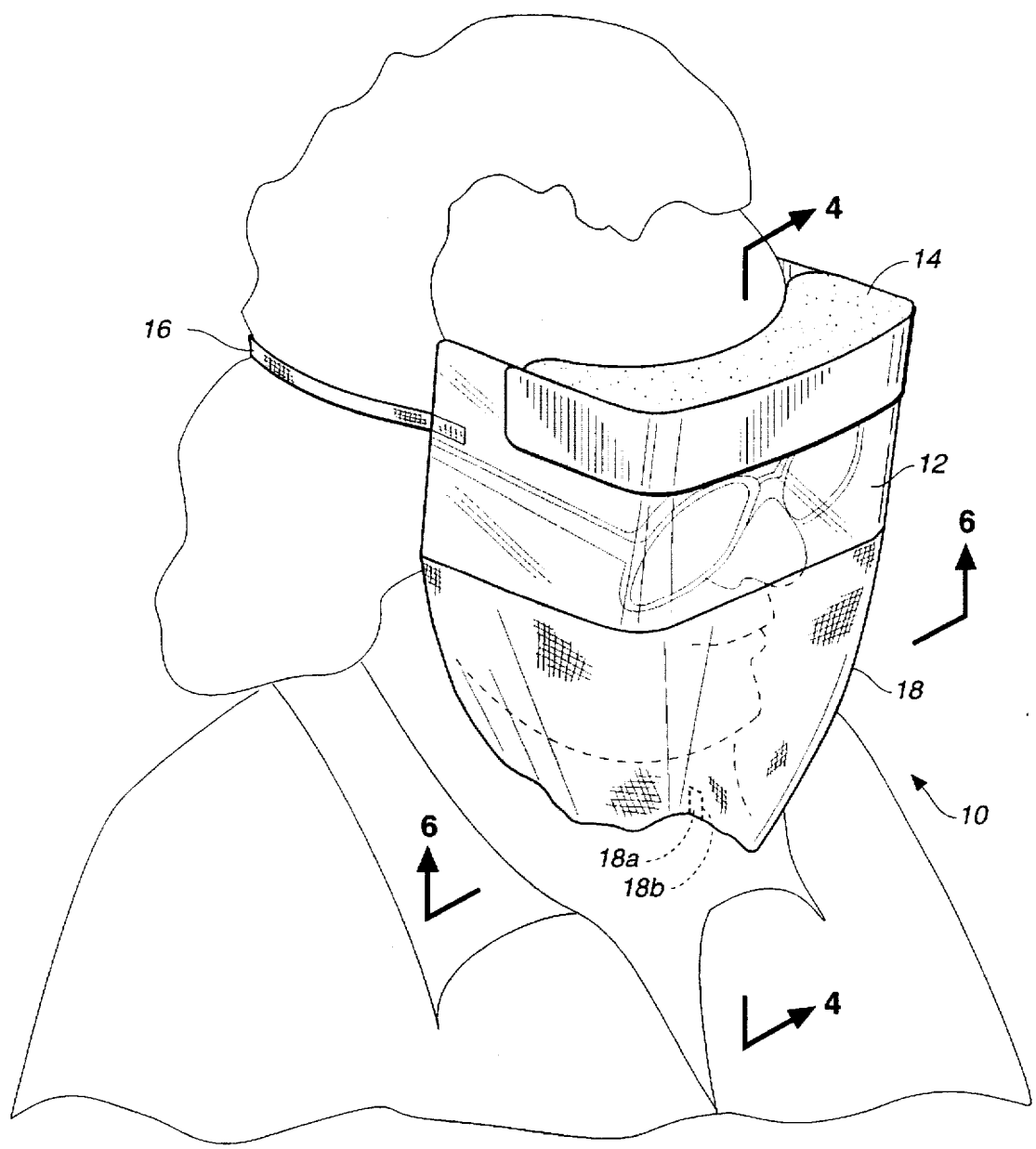
FIG._2

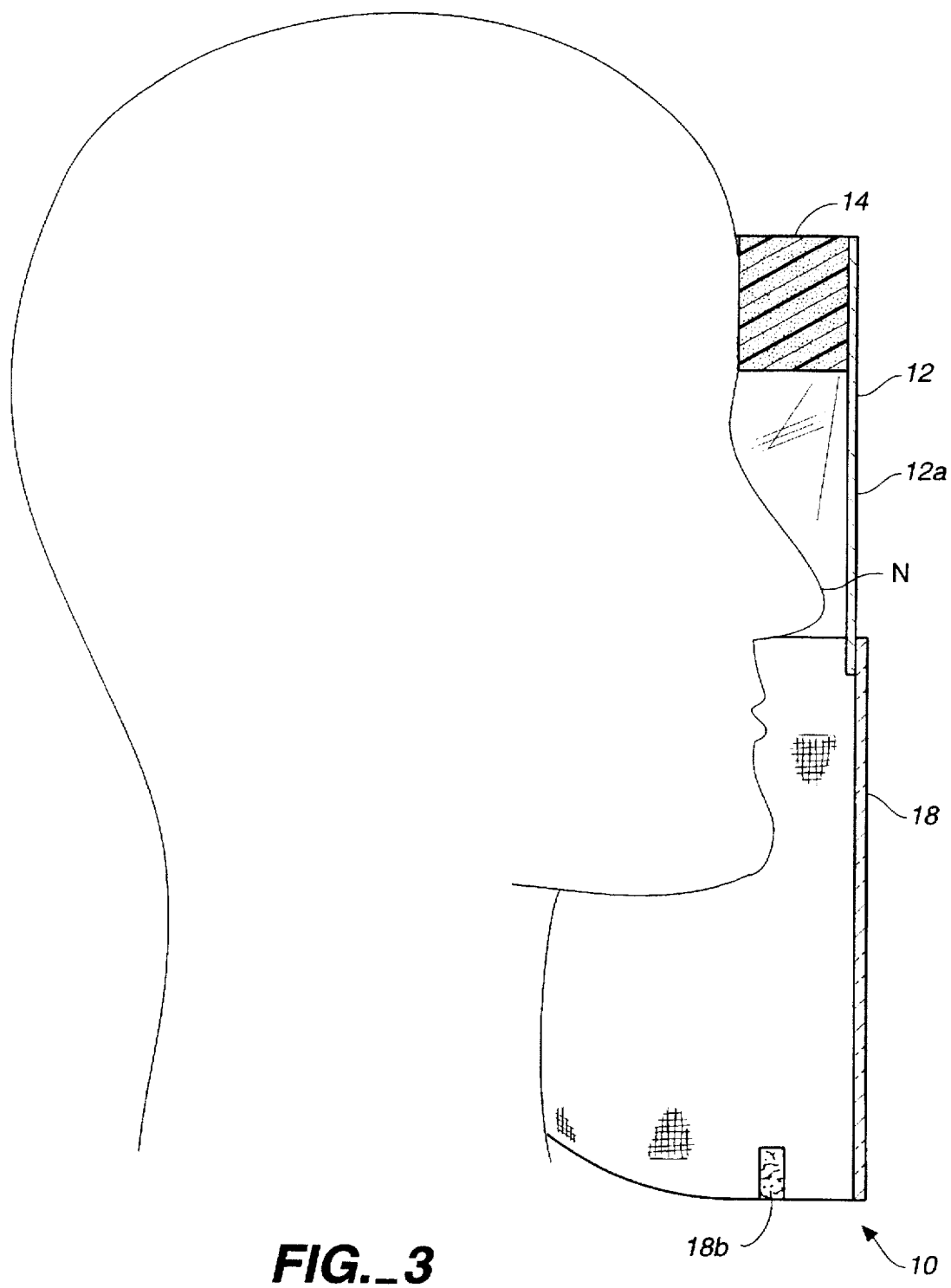
FIG._3

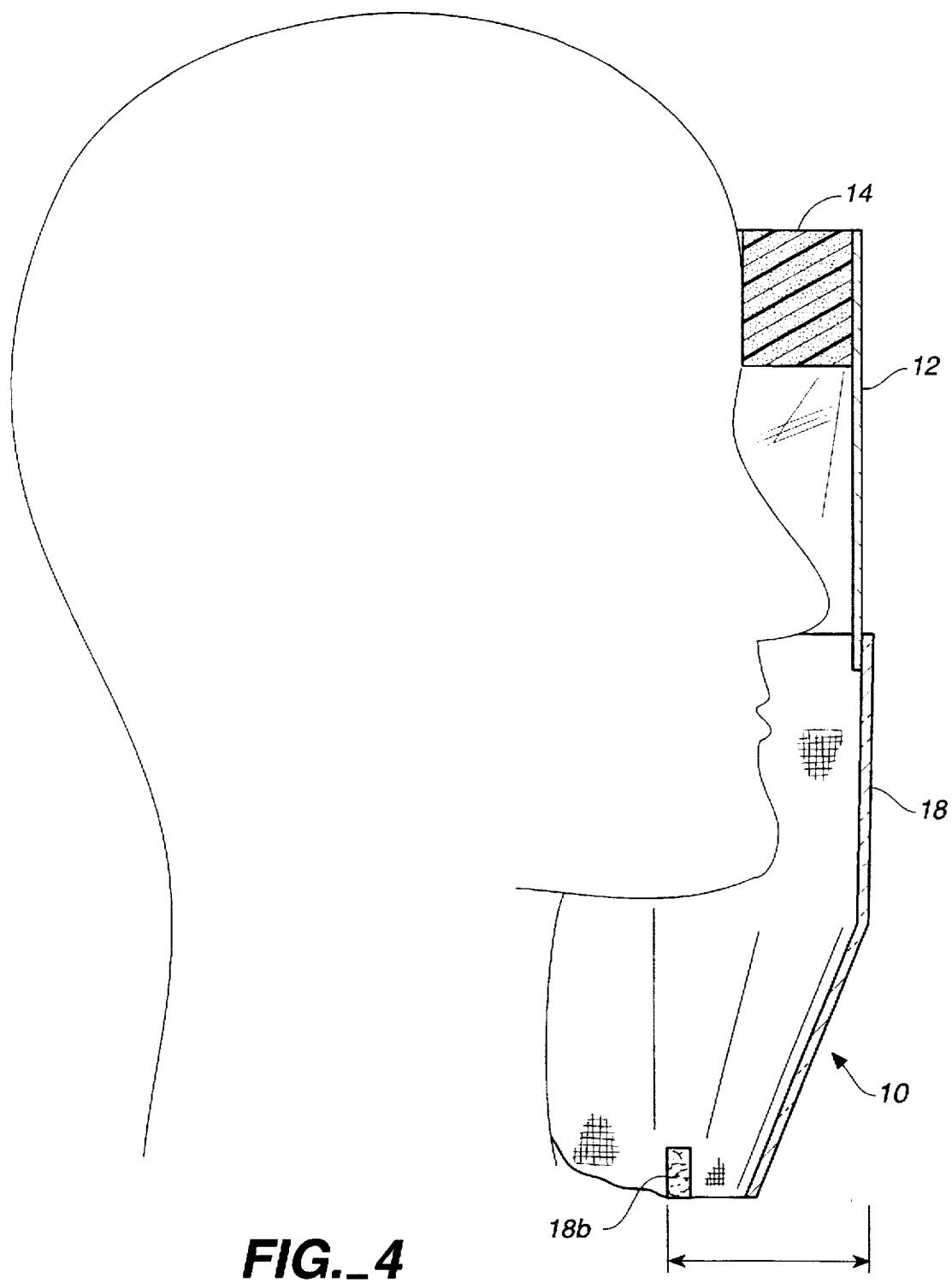
FIG._4

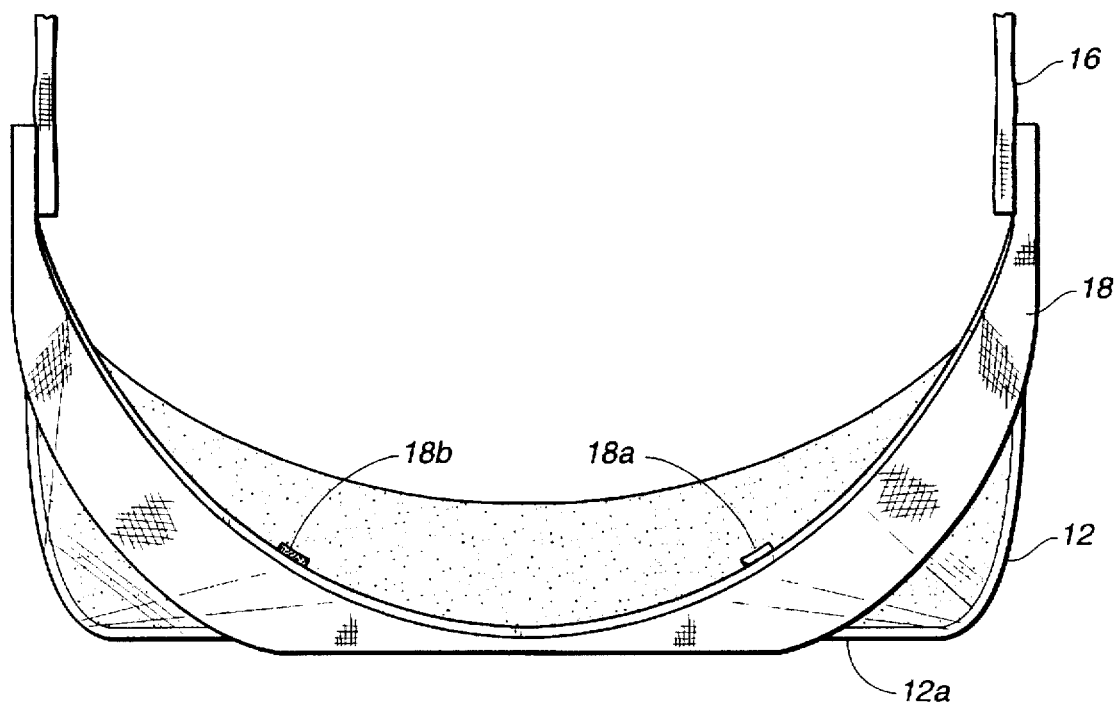
FIG._5
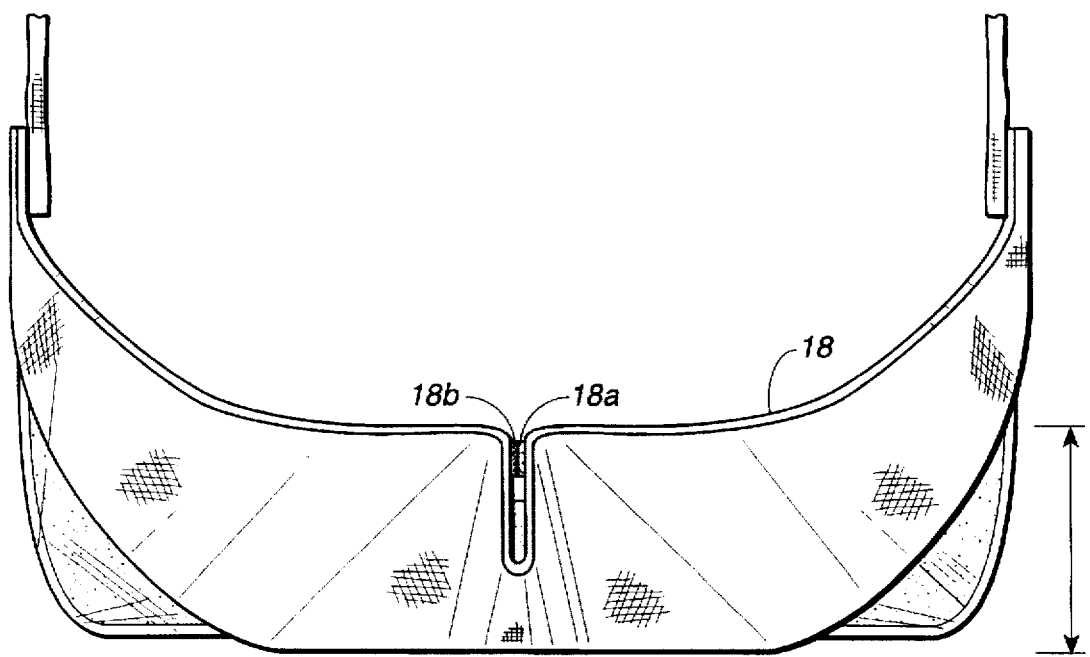
FIG._6

FACE SHIELD HAVING CLOSEABLE DRAPE

BACKGROUND OF THE INVENTION

1. Field of the Invention

This invention is an improved face shield apparatus providing improved protection for the user's face from splashes of bodily fluids, and other foreign materials.

2. Description of the Prior Art

Face shields are routinely worn in hospital operating room and emergency room environments. Such shields are designed to prevent foreign materials such as blood from splashing into or otherwise contacting the user's face, and particularly the user's eyes, nose and mouth. Known face shields typically consist of a flexible, transparent shield portion made of clear plastic or similar material sized to generally cover the user's face, a flexible forehead spacer portion made of foam or similar material for contact with the wearer's forehead to provide adequate clearance of the transparent flexible shield portion away from the user's face, and a headband worn around the head for securing the face shield to the user's head. When worn, the flexible forehead spacer portion substantially seals the top portion of the shield to prevent spatters from reaching the user's face from the top, and the flexible transparent shield portion prevents spatters from reaching the user's face from the front. Full-face shields may not adequately protect the user's mouth, chin and neck area.

Some face shield products further incorporate a fabric material attached to the lower edge of a half-sized shield, fan-folding the fabric from a closed position adjacent the lower edge of the shield to an extended position at least partially covering the user's mouth and chin area. However, known face shields still do not provide adequate protection to the user's neck and chin area. Thus, there is a need for a face shield which will adequately protect the user. Current shields in the medical profession, in particular, do not provide the protection afforded by the present invention.

SUMMARY OF THE INVENTION

The face shield apparatus of this invention provides an apparatus to protect the user's face from exposure to foreign materials. The face shield apparatus will protect the user's face in medical settings as proscribed by the 1991 Occupational Safety and Health Administration's regulation 29 CFR Part 1910.1030, Occupational Exposure to Bloodborne Pathogens; Final Rule. In non-medical use, this invention relates generally to preventing non-impact exposure to liquid splash and dust during the course of activities such as but not limited to, painting, gardening, woodworking, automotive, food preparation, and general assembly line work where dust and spray are likely to occur. This invention is an improved face shield apparatus providing improved protection for the user's face from splashes of bodily fluids, and other foreign materials.

The inventive shield apparatus includes a transparent face portion providing a flat viewing area in front of the user's eyes, thus minimizing optical distortion and glare. The transparent face portion is preferably in the form of a flexible sheet made from crystal clear, anti-fog plastic to provide excellent visibility. A forehead barrier portion protects the user against splash to the eyes from above, and consists of a self-shaping foam headpiece which molds to the forehead, while holding the transparent face portion far enough off of the user's face to allow the user to wear glasses, as well as to enhance the circulation of cooling air to the user's face.

A head strap portion is connected to the transparent face portion, and is adapted to fit around the user's head to hold the face shield in place. A lower drape portion is releasably attached to the lower edge of the transparent face portion, and protects against splash coming up under the shield. This drape portion features a fluid-impermeable fabric below the plastic to cover the user's chin and upper neck. Light pressure to the bottom of the fluid barrier fabric closes the fabric under the user's chin with hook-and-loop type or other fasteners. The fabric can be opened or closed to allow the fabric to hang freely, or close snugly under the user's chin. Users wearing mouth masks receive extra protection against soak-through from the inclusion of this barrier fabric in front of the mask. In addition, the fluid barrier fabric is not permanently affixed to the transparent face portion, but can be removed by a firm tug. The drape portion fasteners can be closed and re-opened as needed.

BRIEF DESCRIPTION OF THE DRAWINGS

FIG. 1 is a perspective view of the face shield apparatus of this invention in use, illustrating the transparent face portion, forehead barrier portion, head strap portion, and fluid-impermeable fabric drape portion, this view illustrating the drape portion in its free-hanging configuration;

FIG. 2 is a perspective view of the inventive apparatus illustrating the fluid-impermeable drape portion in its closed configuration with fasteners attached;

FIG. 3 is a side elevation cross-sectional view of the inventive apparatus in its free-hanging configuration, this view taken along line 3—3 of FIG. 1;

FIG. 4 is a side elevation cross-sectional view of the inventive apparatus in its closed configuration, this view taken along line 4—4 of FIG. 2;

FIG. 5 is a bottom plan view of the inventive apparatus in its free-hanging configuration, this view taken along line 5—5 of FIG. 1; and FIG. 6 is a bottom plan view of the inventive apparatus in its closed configuration, this view taken along line 6—6 of FIG. 2.

DETAILED DESCRIPTION OF A PREFERRED EMBODIMENT

FIG. 1 is a perspective view of the face shield apparatus 10 of this invention in use, illustrating the transparent face portion 12, connected to the forehead barrier portion 14, head strap portion 16, and fluid-impermeable fabric drape portion 18, this view illustrating the drape portion 18 in its free-hanging configuration, with fasteners 18a, 18b separated. In this position, the drape portion serves to cover the user's mouth, chin and neck with a fluid-impermeable fabric to prevent foreign material such as spattered blood from contacting the user. The preferred material is generally impermeable to fluids, but permits passage of air around its edges. Furthermore, this free-hanging shape permits air circulation around the user's face.

Transparent face portion 12 is preferably made of high quality, anti-fog plastic, of a size to generally extend from the user's forehead to just below the user's nose. Types of plastic materials useful for the face portion that are optically clear, thin gauge plastics such as PVC, PET, PETG, OPS, Polycarbonate and APET. These are all rolled or sheet plastics that can be used for making face shields. The face portion is designed so that when it is in place on the users face, optical area 12a in front of the user's eyes is generally flat, thus creating less optical distortion to the user.

Fabrics that can be used to create the drape barrier below the plastic shield can fall into three general categories; knits, wovens, or non-wovens. These fabrics can be manufactured by various methods such as: spun bonding, thermal bonding, chemical bonding, melt blown, spun laced or hydro entangled, and Tyvek. All of these fabrics can be made to have degrees of barrier protection against liquid penetration. That barrier protection can range from repellent to impermeable. In general, a lower degree of protection is afforded by repellent fabric.

Repellent will repel unless fluid on the fabric is subjected to pressure. Under pressure, fluid will pass through the fabric. The barrier protection is attained by laminating a film to the back of the fabric. Various materials such as EVA, PVA, polyethylene and polyurethene can be used as films. For example, the apparatus may utilize a laminated spunbound polypropylene fabric with a LDPE film. The barrier fabric is fluid impermeable and will not ignite when exposed to fire, but rather melts.

FIG. 2 is a perspective view of the inventive apparatus 10 illustrating the fluid-impermeable drape portion 18 in its closed configuration with fasteners 18a, 18b attached together. These fasteners preferably consist of complementary pieces of hook-and-loop fastener material, so that they may be engaged and disengaged with little effort. Alternatively, other types of fasteners could be employed, such as clips, snaps, tape, adhesive, loops with eye catches, or the like. Fasteners can be used in multiple configurations (more than one fastener) and positioning can be altered on the surface of the fabric to create different degrees of closure. This closed configuration may be preferred as more comfortable by some users, and may offer more substantial protection to the user's mouth and chin area.

FIG. 3 is a side elevation cross-sectional view of the inventive apparatus 10 in its free-hanging configuration, this view taken along line 3—3 of FIG. 1. This view illustrates the desired spacing of the face portion 12 from the user's nose, achieved by proper sizing of forehead barrier 14. Also, this view illustrates the relatively large volume of air shielded behind drape portion 18 and around the user's chin and neck area, thus allowing better air circulation for comfort.

FIG. 4 is a side elevation cross-sectional view of the inventive apparatus 10 in its closed configuration, this view taken along line 4—4 of FIG. 2. This view illustrates the relatively smaller volume of air shielded behind drape portion 18 and around the user's chin and neck area, but providing a more confined and rigid barrier for the user, which may be desirable in certain situations.

FIG. 5 is a bottom plan view of the inventive apparatus 10 in its free-hanging configuration, this view taken along line 5—5 of FIG. 1. This view illustrates the desired flat surface achieved by proper design of optical portion 12a.

FIG. 6 is a bottom plan view of the inventive apparatus 10 in its closed configuration, this view taken along line 6—6 of FIG. 2. This view illustrates the gathering and "darting" of the drape portion 18 by the fastening of fasteners 18a, 18b.

Shield dimensions for the plastic and fabric can vary in length, width, and gauge of plastic. For example, the plastic may be 5.5×13 inches and of a 7 mil gauge (0.007), while the fabric may be 5.0×13 inches. Both the plastic and fabric may have radial cut corners to remove sharp edges and soften the looks. Altering the size, or dimensions, of the plastic and fabric will not change the intent of this shield apparatus. Alterations can he minor, such as the angle of radial corners on the plastic or fabric, and do not serve to change the protection provided.

Foreign materials the shield apparatus protects against includes blood and other bodily fluids, dust, dirt, chemicals found in medical and industry, sprays, paint, oils, sawdust, and garden sprays. In addition, the apparatus may be used in industry for clean room assembly.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims and equivalents.

What is claimed as invention is:

1. A face shield apparatus to prevent bodily fluids and other foreign materials from splashing into a user's face, said face shield apparatus comprising:

a transparent face portion including a generally flat viewing area, said face portion having an upper edge and a lower edge;

a forehead barrier portion connected to said transparent face portion upper edge, said forehead barrier portion adapted to provide a barrier to protect the user against splash to the user's eyes from above;

a head strap portion connected to said transparent face portion, said head strap portion adapted to fit around the user's head to hold said face shield in place; and a lower drape portion releasably attached to said lower edge of said transparent face portion, said lower drape portion including a pair of fasteners enabling said lower drape portion to be opened or closed, said lower drape portion adapted to protect the user against splash coming up under the shield.

2. The face shield apparatus of claim 1 wherein said fasteners comprise hook-and-loop fasteners.

3. The face shield apparatus of claim 1 wherein said lower drape portion comprises a fluid-impermeable fabric to cover the user's chin and upper neck.

4. The face shield apparatus of claim 1 wherein said drape portion comprises non-woven, impermeable barrier fabric of laminated spunbound polypropylene fabric with an LDPE film.

5. The face shield apparatus of claim 1 wherein said transparent face portion is composed of a material selected from the group consisting of PVC, PET, PETG, OPS, Polycarbonate and APET.

* * * * *